(12) United States Patent
Conner

(10) Patent No.: US 8,888,550 B1
(45) Date of Patent: Nov. 18, 2014

(54) AIRBORNE SCENT DISPENSING APPARATUS AND SYSTEM

(76) Inventor: James C. Conner, Oklahoma City, OK (US)

( * ) Notice: Subject to any disclaimer, the term of this patent is extended or adjusted under 35 U.S.C. 154(b) by 88 days.

(21) Appl. No.: 13/573,121

(22) Filed: Aug. 23, 2012

Related U.S. Application Data

(60) Provisional application No. 61/575,581, filed on Aug. 24, 2011.

(51) Int. Cl.
*A63H 33/28* (2006.01)
*A01M 31/00* (2006.01)
*A61L 9/14* (2006.01)

(52) U.S. Cl.
CPC .............. *A01M 31/008* (2013.01); *A61L 9/145* (2013.01)
USPC .......................................................... 446/15

(58) Field of Classification Search
CPC ................................ B05B 11/30; B05B 15/007
USPC .......................................................... 446/15
See application file for complete search history.

(56) References Cited

U.S. PATENT DOCUMENTS

| | | | | |
|---|---|---|---|---|
| 3,046,192 A | * | 7/1962 | Bilyen | 239/9 |
| 4,159,672 A | * | 7/1979 | Garguilo et al. | 454/337 |
| 5,048,218 A | * | 9/1991 | Stewart | 43/1 |
| 5,610,674 A | * | 3/1997 | Martin | 352/85 |
| 5,857,281 A | * | 1/1999 | Bergquist et al. | 43/1 |
| 5,924,597 A | * | 7/1999 | Lynn | 222/1 |
| 6,325,475 B1 | * | 12/2001 | Hayes et al. | 347/2 |
| 6,339,897 B1 | * | 1/2002 | Hayes et al. | 43/132.1 |
| 6,379,242 B1 | * | 4/2002 | Wiseman et al. | 454/337 |
| 6,443,434 B1 | * | 9/2002 | Prather | 261/26 |
| 6,550,689 B1 | * | 4/2003 | Hoyes et al. | 239/1 |
| 6,584,633 B2 | * | 7/2003 | Chute et al. | 8/158 |
| 6,589,487 B1 | * | 7/2003 | Ly et al. | 422/125 |
| 6,712,286 B2 | * | 3/2004 | Baxter et al. | 239/36 |
| 6,871,595 B1 | * | 3/2005 | Lewis | 102/502 |
| 7,223,166 B1 | * | 5/2007 | Wiseman et al. | 454/337 |
| 7,696,635 B2 | * | 4/2010 | Boone | 290/55 |
| 7,898,407 B2 | * | 3/2011 | Hufton et al. | 340/539.11 |
| 7,921,578 B2 | * | 4/2011 | McAllister et al. | 34/597 |
| 8,048,436 B1 | * | 11/2011 | Whitworth | 424/411 |
| 8,102,071 B2 | * | 1/2012 | Catlin | 290/54 |
| 8,206,697 B1 | * | 6/2012 | Schmidt | 424/84 |
| 2003/0034403 A1 | * | 2/2003 | Baxter et al. | 239/36 |
| 2004/0064995 A1 | * | 4/2004 | Gilmore | 43/1 |
| 2007/0095941 A1 | * | 5/2007 | Gorres | 239/337 |
| 2012/0317863 A1 | * | 12/2012 | Buck | 43/2 |

* cited by examiner

*Primary Examiner* — Kurt Fernstrom
*Assistant Examiner* — Dolores Collins
(74) *Attorney, Agent, or Firm* — Martin G. Ozinga; Phillips Murrah PC

(57) ABSTRACT

The present invention comprises an attractant and or cover scent bubble delivery device, system, and method of utilizing same wherein bubbles are generated with a desired attractant, scent and or other chemical in a timed and or desired manner remotely such that airborne bubbles may be utilized to attract desired wild life and or provide a cover scent for the user.

1 Claim, 3 Drawing Sheets

AIRBORNE SCENT DISPENSING APPARATUS AND SYSTEM

CROSS-REFERENCE TO RELATED APPLICATIONS

Priority is claimed from provisional patent application U.S. Ser. No. 61/575,581 filed on Aug. 24, 2011, and incorporated by reference herein.

BACKGROUND OF THE INVENTION

1. Field of the Invention

In general, the present invention relates to an animal attractant and or cover scent dispersal apparatus and system associated with hunting. More particularly, the present invention relates to a new and improved animal attractant device, system and method of using the same for utilizing airborne bubbles to carry an animal attractant and or cover scent throughout a desired location as desired. It is understood that the current invention may be used to disperse desired odors and or chemicals for non-hunting applications.

2. Description of the Prior Art

Game animals such as deer and the like are known to be attracted during mating season by certain scents classified as pheromones. In the case of a doe, the pheromone is contained in her urine which is sprinkled on the ground as a means of notifying a buck of her availability. Chemists and others have developed both artificial and natural scents which substantially duplicate the smell of doe-in-estrus urine. Such liquid scents are offered in small quantities and at high cost.

Furthermore, game animals are sensitive to the odor of humans. Accordingly, hunters need to disguise their scent trail. In hunting deer, doe urine can be used for that purpose. A properly applied trail of doe urine, in addition to masking the hunter's scent, may also attract a buck towards the hunter who lies in wait.

One of the most common dispensers for liquid scent is a drag rag. For covering a trail with a drag rag, a hunter applies liquid scent to an absorbent pad which is then dragged behind him as he walks. By applying the scent in this manner, the scent rubs off on the trail and is applied in a manner simulating the natural method of scent presentation by a doe but as the rag is dragged, the scent is diluted. This results in a strong scent at the beginning and a weak scent trailing off at the end. If a buck crosses the hunter's trail, he is just as likely or more likely to head away from the hunter than towards him as the trail tapers stronger towards where the hunter began.

There are dispensers that hook to the branch of a tree for dripping liquid scent on the ground and there are dispensers that spray the liquid scent into the air where it dissipates quickly. These devices are obviously limited to relatively small dispersal patterns and therefore, have limited ability to be noticed by the desired game.

The above discussion is not to be considered exhaustive. It does, however, demonstrate that a need exists for a new and improved scent dispersing system over the known prior art devices that have had very little changes since the conception of the same. The consuming industry is looking for solutions, methods, and systems to address these needs and there is an obvious need to fill the gap where the prior art has failed. What is needed is an apparatus, system and method to address these shortcomings in the prior art while providing a superior design. Thus, there is a need for a new and improved scent delivery system. The current invention provides a superior product where the prior art fails.

SUMMARY OF THE INVENTION

In view of the foregoing disadvantages inherent in the known types of scent application devices now present in the prior art, the present invention provides a convenient, easily transported, and durable construction. As such, the general purpose of the present invention, which will be described subsequently in greater detail, is to provide a new and improved cover scent and or attractant dispersal device, system, and method which has all the advantages of the prior art and none of the disadvantages.

It is contemplated that the invention generates bubbles that may disperse a desired scent and or animal attractant by utilizing the air travel of a bubble that has a mix of the scent and or attractant. It is further contemplated the current invention may be mounted such that the bubble generator may swivel according to wind currents, utilize a timer for activation, and or a remote control for activation. It is contemplated that the invention may be used with hunting or other applications, such as but not limited to night clubs where it is desired to have an aesthetically pleasing smell and or deodorizing element mixed with a bubble delivery system for dispersal.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in this application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting. As such, those skilled in the art will appreciate that the conception upon which this disclosure is based may readily be utilized as a basis for the designing of other structures, methods, and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

Therefore, it is an object of the present invention to provide a new and improved attractant and or scent bubble delivery system that may be utilized with hunting for the attraction of animals where the prior art fails.

It is a further object of the present invention to provide a new and improved attractant and or scent bubble delivery system which is of a durable and reliable construction and may be easily and efficiently manufactured and marketed.

An even further object of the present invention is to provide a new and improved attractant and or scent bubble delivery system and method of constructing the same which is susceptible to a low cost of construction with regard to both materials and labor, and which accordingly is then susceptible to low prices of sale to the consuming public, thereby making such invention economically available to those in the field and public in general.

Still another object of the present invention is to provide a new and improved attractant and or scent bubble delivery system which provides all of the advantages of the prior art, while simultaneously overcoming some of the disadvantages normally associated therewith.

While still another object of the present invention is to provide a new and improved attractant and or scent bubble delivery system which allows for a timed and or remote release of bubbles as desired.

It is a further object of the present invention to provide a new and improved attractant and or scent bubble delivery system which may freely rotate with wind directions for a more optimal release of bubbles in the direction of the blowing wind.

Furthermore, it is a further object of the present invention to provide a new and improved attractant and or scent bubble delivery system which is light weight, battery operated, and easy to fill with the desired attractant and or scent.

Still furthermore, it is a further object of the present invention to provide a new and improved attractant and or scent bubble delivery system which may be utilized to disperse aesthetically pleasing scents for such locations as department stores, movie theatres, concerts and so forth as well as novelty smells.

Yet another object of the present invention is to provide a new and improved attractant and or scent bubble delivery system that may be mounted to a tree and or tripod which allows for rotation with wind direction as well as fixed positions as desired.

Still another object of the present invention is to provide a new and improved attractant and or scent bubble delivery system that may utilized to disperse other chemical such as deodorizes, cleansers, and repellents.

It is a further object of the present invention to provide a new and improved attractant and or scent bubble, delivery system that is relatively quiet such that animals are not alerted and or frightened by same.

These, together with other objects of the invention, along with the various features of novelty which characterize the invention, are pointed out with particularity in the claims annexed to and forming a part of this disclosure. For a better understanding of the invention, its operating advantages, and the specific objects attained by its uses, reference should be had to the accompanying drawings and descriptive matter in which there are illustrated preferred embodiments of the invention.

The present invention referred to throughout may be embodied in other specific forms without departing from its spirit or essential characteristics. The described embodiments are to be considered in all respects only as illustrative and not restrictive. Furthermore, each of the methods that have been described should also be considered only as illustrative and not restrictive.

BRIEF DESCRIPTION OF THE PICTORIAL ILLUSTRATIONS, GRAPHS, DRAWINGS, AND APPENDICES

The invention will be better understood and objects other than those set forth above will become apparent when consideration is given to the following detailed description thereof. Such description makes reference to the annexed pictorial illustrations, graphs, drawings, exhibits and appendices herein.

DETAILED DESCRIPTION OF THE PREFERRED EMBODIMENTS

Figure 1:
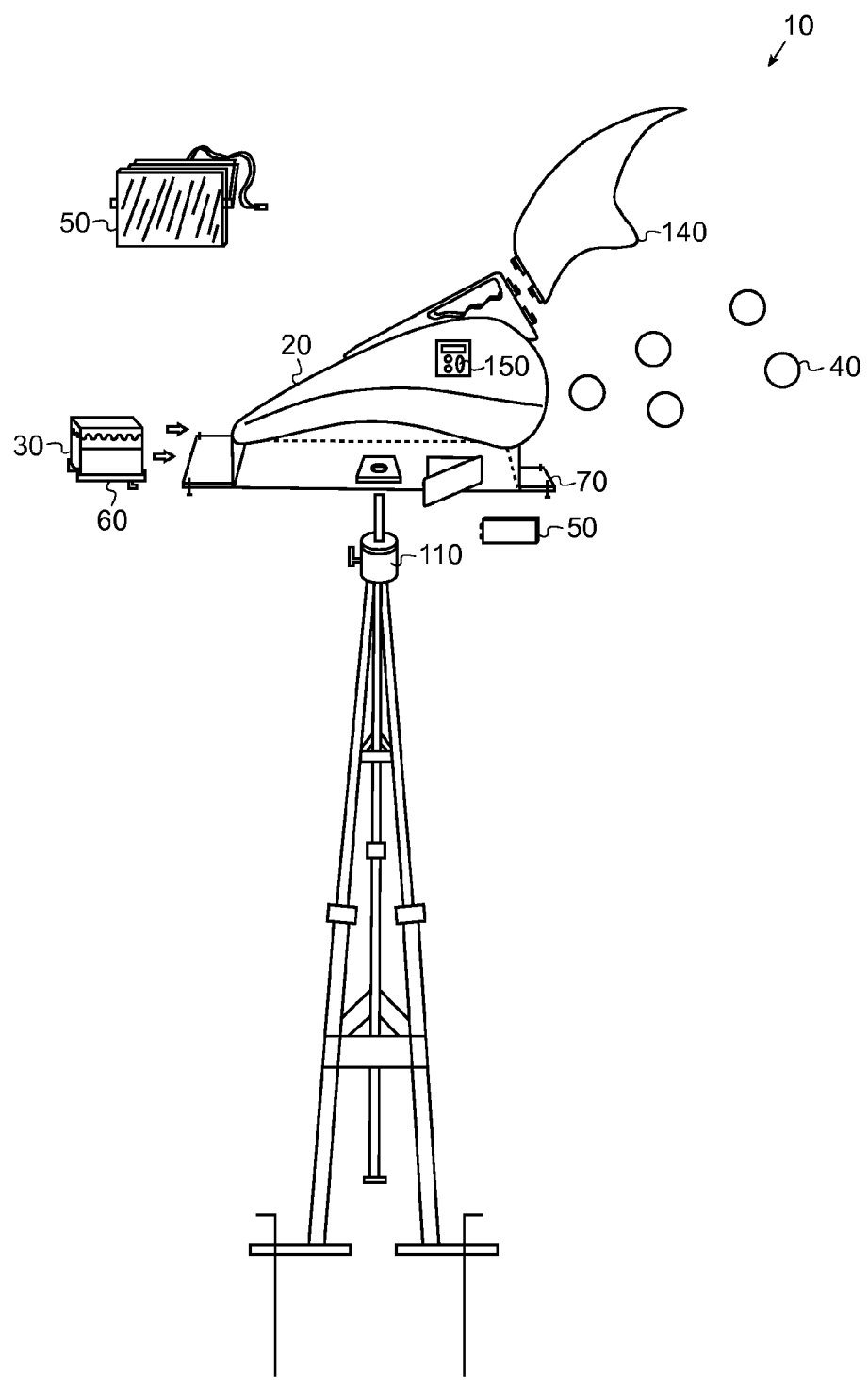
FIG. 1 is a general depiction of a preferred embodiment in accordance with the present invention.
Figure 2:
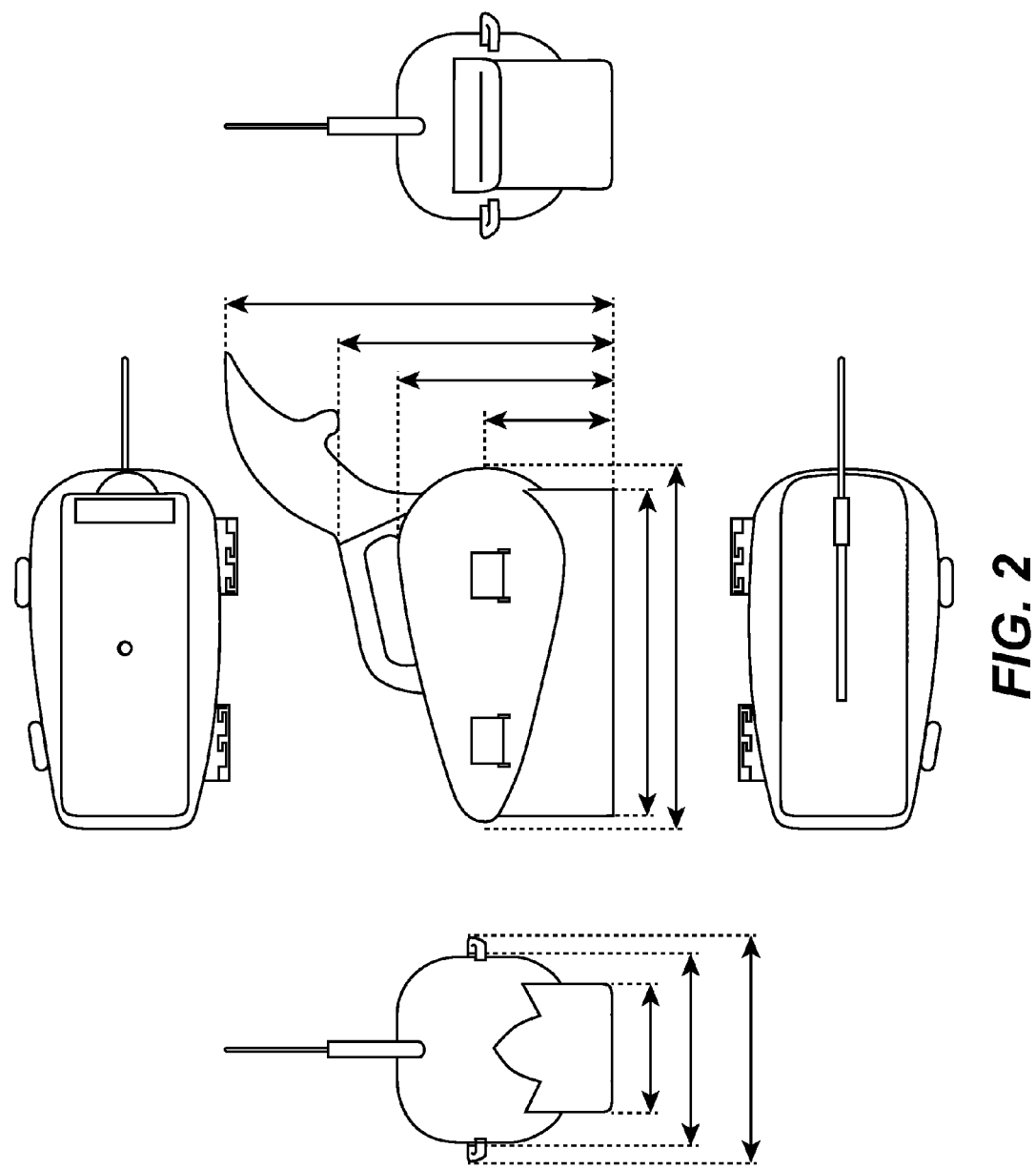
FIG. 2 is a general depiction of a preferred embodiment of a generator in accordance with the present invention.
Figure 3:
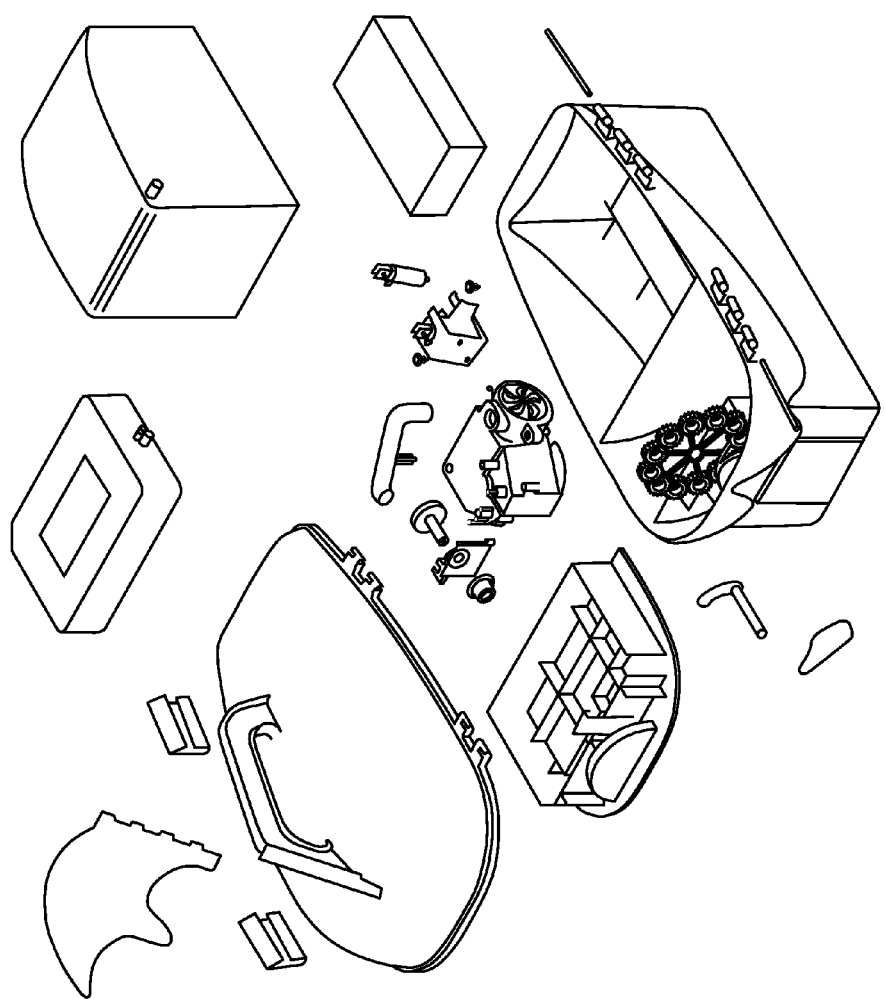
FIG. 3 is a general depiction of a preferred embodiment of a generator in accordance with the present invention.

Referring now to the drawings, wherein like reference numerals designate corresponding structure throughout the views, and referring in particular to FIG. 1, reference numeral 10 generally refers to a new and improved attractant and or cover scent bubble delivery device, system, method, and combinations thereof, hereinafter referred to collectively as invention 10, in accordance with the present invention. It is understood that invention 10 may be a delivery system for other than hunting applications, attractants, and or scents such as but not limited to deer, elk, hog, bear, and moose. It is also contemplated to provide invention 10 for use with predators in general.

It is also contemplated invention 10 may be a delivery system for applications where it is desired to disperse chemical in an airborne manner, such as deodorizers, fragrances, and so forth. Still further, it is contemplated that invention 10 may have military uses as well as crowd control uses such as but not limited to delivery of neurotoxins, tear gas, and so forth.

Invention 10 may comprise bubble generator 20 wherein a desired fluid 30 is utilized to create bubbles 40 for dispersing. Generator 20 may comprise a power source 50 such as but not limited to a battery pack, a rechargeable battery back, hard wired, and combinations thereof. It is also contemplated to provide a solar panel for battery recharge and or operating invention 10.

Fluid 30 may be an animal attractant sent, fragrance, novelty smell and so forth. It is contemplated that bubbles 40 may be a 20/80 ration of desired scent to bubble formula known in the art. It is also understood that numerous mixtures are contemplated such as but not limited to a 50/50 ratio as well as greater or lesser ratios, as well as multiple mixes.

Fluid 30 may be provided in a replaceable cartridge 60 and provide a seal for the containment of unwanted fluid leakage. Generator 20 may also have a closable aperture 70 to also prevent unwanted leakage of fluid 30 and associated scent from escaping generator 20 when not in use. Generator 20 may provide a pump 80 for moving fluid 30 from cartridge 60 to wheel 90 along with a motor unit 100 for moving wheel 90 along with operating pump 80. Fluid 30 cartridges may be in multiple sizes such as but not limited to ½ pint, pint cartridge, and quart cartridges. It is contemplated that cartridges 60 may be refillable or non-refillable.

It is also understood that generator 20 may include a sound muffling system to quit operations of generator 20. It is also contemplated that a sound effect device may be include such as but not limited to a game calling system that mimics desired sounds utilized in hunting. Furthermore, it is contemplated to provide a camera system which may include an audio for remote listening and viewing.

Generator 20 may be mounted on swivel 110 such that generator 20 may move freely with wind direction. Swivel 20 may be mounted to tripod 120, tree mounting unit 130, hunting blind and other forms of mounting that allow for the rotation of generator 20 with wind direction. Invention 10 may also include a removable wind fan blade 140. It is understood that invention 10 may be hand held, swivel mounted, tree mounted, tree swivel mounted, tripod swivel mounted, blind mounted, truck mounted and so forth with combinations thereof.

Generator 20 may be of numerous sizes such as but not limited to a back pack size or hand held size, larger industrial size for larger quantities and events such as continuous use at a nightclub, and even a larger size for events such as a football games or concert. Invention 10 may be colored for concealment such as flat black, camouflage in general, glossy three color fade, and so forth.

It is contemplated that bubbles 40 may travel with the wind to spread scent and it understood that the bubbles may carry up to 150 yards and further depending on wind and weather conditions. It is understood that the scent may be reach farther than the actual airborne bubble and the dispersal is not limited to just the flight path of a bubble.

It is further contemplated that invention 10 may include a timer 150 for the time release of fluid 30 as desired. It is also contemplated that invention 10 may utilize a remote control for selective activation as desired. A remote control can be wired, wireless, and combination thereof. For the purpose of conserving an expensive liquid scent, generator 20 could be programmed in several modes, one of which is a manual mode that times the dispersal in addition to an automatic mode which provides dispersal at preset intervals.

It is contemplated invention 10 is generally portable such that it can carried by a hunter, that is programmable to disperse at timed intervals or as desired remotely over a large distance and that can be used in a fixed location after arrival at a hunting site. A number of implementations have been described herein. Nevertheless, it will be understood that various modifications may be made.

Accordingly, other implementations are within the scope of the following claims. Changes may be made in the combinations, operations, and arrangements of the various parts, elements, and amounts described herein without departing from the spirit and scope of the invention. From the foregoing description of the preferred embodiment of the invention, it will be apparent that many modifications can be made, and it will be understood that the presently disclosed embodiment is exemplary only, and that the invention is not limited thereto.

I claim:

1. An animal attractant scent bubble delivery generator comprising:
   a housing having a top, a bottom, an interior; an exterior, an access panel on said exterior for accessing said interior, an aperture from said interior to said exterior for releasing bubbles from said interior;
   a tripod swivelly mounted to said bottom of said housing;
   a wind fan blade removably attached to said top of said housing for swiveling said housing on said tripod according to wind direction;
   a battery powered bubble generator for generating said bubbles wherein said generator is positioned in said interior of said housing and attached to said aperture for releasing said bubbles from said interior of said housing; and
   a cartridge for holding animal attractant scent liquid wherein said cartridge is removably in communication with said generator and said fluid can into said generator for creating said bubbles and wherein said cartridge is accessible from said access panel on said housing.

* * * * *